Figure 1:
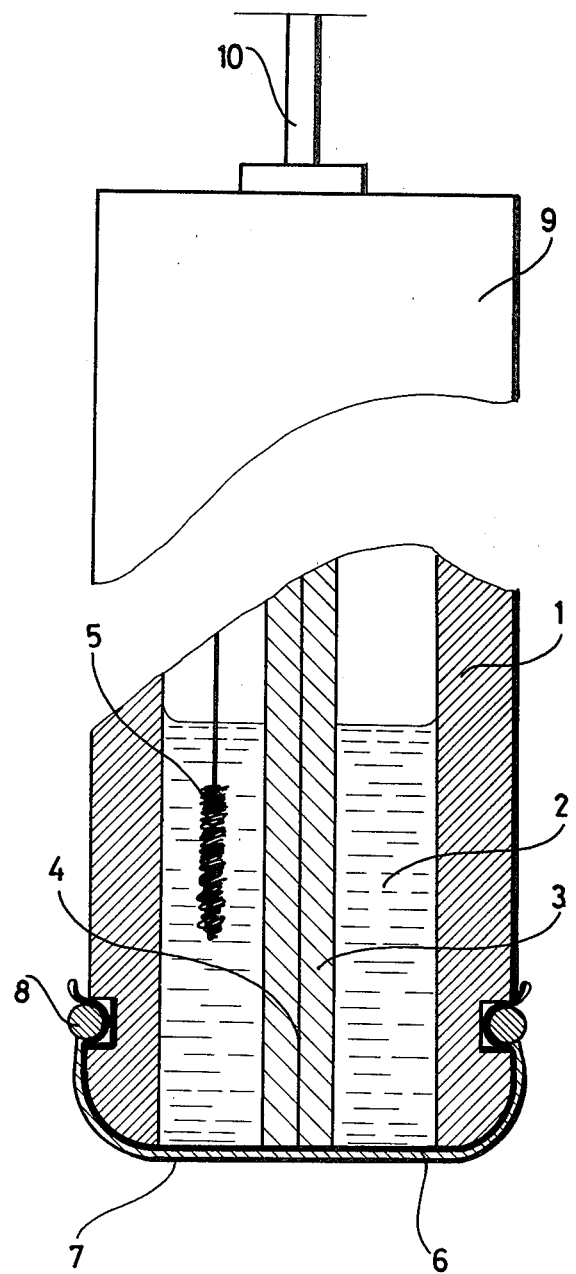

United States Patent [19]

Pungor et al.

[11] 4,354,913
[45] Oct. 19, 1982

[54] MOLECULE SELECTIVE ENZYME ELECTRODE

[75] Inventors: Ernö Pungor; Jenö Havas; Géza Nagy; Emma Porjesz, all of Budapest, Hungary

[73] Assignee: Radelkis Elektrokémiai Müszergyártó Szövetkezet, Budapest, Hungary

[21] Appl. No.: 218,104

[22] Filed: Dec. 19, 1980

Related U.S. Application Data

[63] Continuation of Ser. No. 49,337, Jun. 18, 1979, abandoned.

[30] Foreign Application Priority Data

Jun. 21, 1978 [HU] Hungary ............................. RA 683

[51] Int. Cl.³ ........................ C12Q 1/00; G01N 27/30
[52] U.S. Cl. ................................. 204/195 P; 204/1 T; 204/195 B; 435/177; 435/288; 435/817
[58] Field of Search ................ 204/195 B, 195 P, 1 E; 435/817, 288, 175, 177

[56] References Cited

U.S. PATENT DOCUMENTS

| | | | |
|---|---|---|---|
| 3,539,455 | 11/1970 | Clark | 204/195 P X |
| 3,843,446 | 10/1974 | Vieth et al. | 435/177 X |
| 3,896,008 | 7/1975 | Keyes | 204/1 T |
| 4,066,512 | 1/1978 | Lai et al. | 435/288 X |
| 4,069,106 | 1/1978 | Stanley et al. | 435/177 |
| 4,092,219 | 5/1978 | Lin et al. | 435/177 X |
| 4,216,065 | 8/1980 | Rechnitz et al. | 204/1 T |

OTHER PUBLICATIONS

Klaus Mosbach, "Methods in Enzymology", vol. 44, Immobilized Enzymes, pp. 710–712, (1976), C & EN, p. 16, Oct. 9, 1978.

Primary Examiner—G. L. Kaplan
Attorney, Agent, or Firm—Gabriel P. Katona

[57] ABSTRACT

A molecule selective sensor has an enzymatically active membrane which is prepared by reacting an enzyme with glutaric aldehyde on the surface of a protein membrane found in nature. Exemplary is the reaction of glucoseoxidase with glutaric aldehyde on the surface of hog intestine membrane.

2 Claims, 2 Drawing Figures

MOLECULE SELECTIVE ENZYME ELECTRODE

This is a continuation of Ser. No. 49,337, filed on June 18, 1979 and now abandoned.

The invention relates to a molecule selective electroanalytical sensor which is suitable for the determination of concentration of compounds e.g. glucose dissolved in sample solutions e.g. blood; and it relates to the procedure for the preparation of molecule selective electroanalytical sensors.

There are well known molecule selective sensors, which are suitable for the determination of concentration of compounds dissolved in liquid samples.

The literature (P. L. Bailey: Analysis with selective electrodes Heyden and Son Ltd. London 1976), discusses in detail the electrochemical behaviour and the application of molecule selective sensors. It is a common property of the known molecule selective sensors, which can be considered as electroanalytical measuring cells, that their electrode body holding ion-selective or metal sensing electrode and reference electrode is placed in a tubular body containing electrolyte solution. The end of this body on the side of the sensing electrode is closed by a cover of a gas or gas and dissolved material permeable film, e.g. dialysis membrane. This film is in contact with a layer containing a catalyst for the component to be determined that is an enzyme physically or chemically bound with polyacrylamide gel layer; or gas or gas and dissolved component permeable film such as cellophane film, in contact with a solution containing selective enzyme in suspension.

In known molecule selective sensors the component to be determined, as for example glucose, and in some cases oxygen, enter by diffusion into the reaction layer containing a selective enzyme such as glucose oxidase and there produce a chemical reaction. The sensing electrode gives a signal which is in a well defined relationship with the concentration or activity of a component taking part in the reaction or produced in it. The local value of the mentioned concentration or activity—if all other important parameters remain constant—depends on the reaction rate which is in a well defined relationship with the concentration of the substrate. By measuring the electric current intensity or cell voltage signal given by the enzyme electrode under steady state conditions, the concentration of the sample can be determined.

The known methods for preparation of molecule selective sensors are circuitous, time consuming procedures, requiring special training and knowledge, which often have uncertain reproducibility.

The most disadvantageous property of known sensors is their short life e.g. a few days or, one week, which is due to the unfavourable construction of the reaction layer.

Another drawback is that the bound enzyme containing gel-layers must be stored at low temperature e.g. $-1°$ to $+2°$ C. while not in use to maintain their activity.

The known electrodes easily get damaged, their mechanical stability is small, response time is long e.g. 2 to 8 minutes. It is a further drawback of them appearing during their use, that gas becomes dissolved in the amperometric sensing electrode; e.g. platinum electrode or an oxide layer is formed on its surface further on metal e.g. silver-impurity or electrically insulating layer is produced all of which decrease the active surface of the sensing electrode, and the signal intensity provided by the sensor.

The object of the invention to provide a molecule-selective electrode construction which can be prepared simply without special knowledge and practice in a short time, in a reproducible way; which further has high mechanical stability, and whose life is several times longer than that of the known sensors, e.g. $\frac{1}{2}$ to 1 year, and the response time of which is short, e.g. 20 to 30 seconds.

The invention is based on that discovery, that a sensor of quality required by the object can be prepared where the enzyme catalyst or catalysts needed for the sensor function are bound on protein based natural structured membrane e.g. intestinal membrane which is a self-supporting protein membrane found in nature, and the activated membrane formed in this way is used to prepare the reaction layer of the sensor. The mechanical stability—in spite of their thin character (10 to 15 $\mu$) which is advantageous from the point of view of response time—of the protein based natural membranes (air bladder of fish, epidermis section of mammalias or reptiles, intestinal membrane or cornea of certain animal species) is excellent because of their structure. The active amino group concentration of the amino acids making up the membranes constant and optimal to bind the enzyme. Sensors usable in wide concentration range and having short response times e.g. 30 to 60 seconds can be prepared. After the enzyme immobilization the activated membranes can be stored dry even at room temperature without significant change of their activity for long time e.g. 0.5 to 1 year.

The water-, gas- and ion permeability of the natural based membranes are useful properties. In addition they behave as an impermeable barrier against compounds of high molecular weight which may interfere with the measurement. These can be the substrate itself or other components being in the sample.

Accordingly, the hysteresis phenomenon usually observed after changing samples of different concentration decreases greatly or completely disappears.

FIG. 1 shows a glucose selective sensor wherein 1 is a covering body or container, 2 is a buffering solution, 3 is a support for a platinum sensing electrode 4, and 5 is a silver-silver chloride reference electrode. Numeral 6 indicates a gas permeable polypropylene film; 7 is a protein membrane occurring in nature containing an immobilized enzyme, 8 is a rubber retaining ring and 9 is a cap. 10 is a cable connected to a power source and also contacts electrodes 4 and 5.

Figure 2:
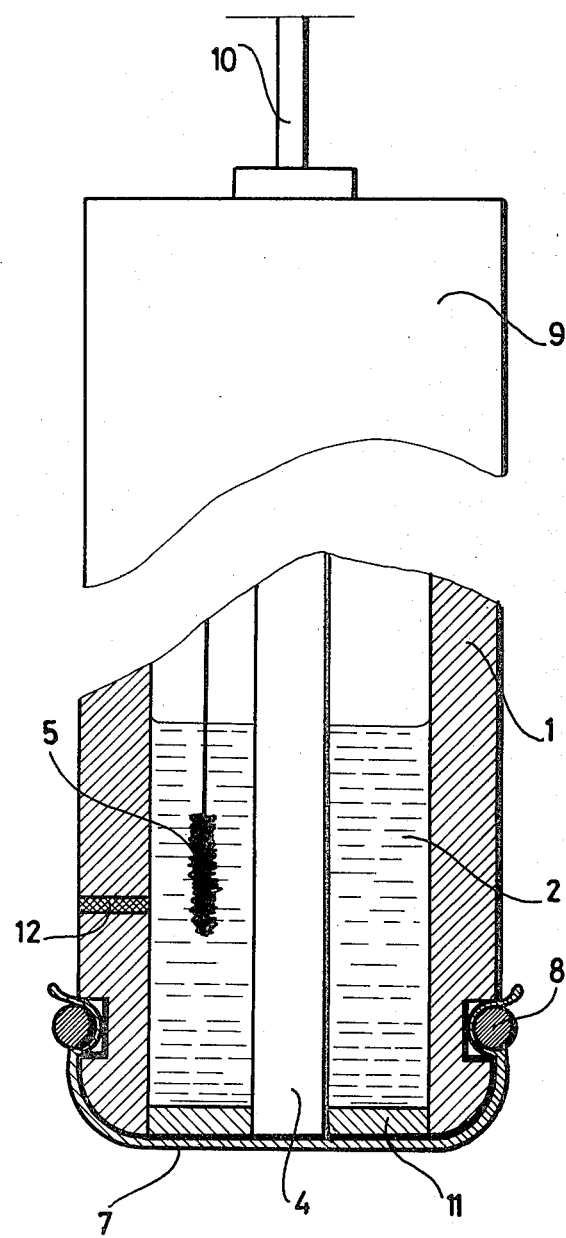

FIG. 2 shows a container 1 having therein a buffer solution 2. Numeral 4 is a sensing electrode and 5 is a reference electrode. 7 is a protein membrane found in nature containing an immobilized enzyme and which is held in place by retaining ring 8. Numeral 11 indicates a disc shaped insulating layer and 12 is a ceramic filter.

The sensor in accordance with the invention can be prepared so the membrane contains two or more different reaction layers; or is made of two or more different enzyme containing membranes disposed one over the other. In this arrangement each membrane surface contains different enzymes in immobilized form. In case of the selective $\beta$-glucoside sensor the membrane surface on the sample side contains $\beta$-glucosidase enzyme while the membrane on the side of the sensing electrode contains glucose oxidase. The enzyme being on the first membrane, the $\beta$-glucosidase, catalyses a hydrolysis reaction between the component to be determined, that is β-glucosidase (e.g. amygdaline, salicine) and the water, and reaction one of the products is glucose. The glucose oxidase enzyme on the other membrane catalyses the reaction between the produced glucose and oxygen. The oxygen provides on the sensing electrode placed behind the membranes a measuring signal proportional to its concentration.

The signal proportional to the decrease of the oxygen concentration is in a well defined relationship with the concentration of the component to be determined.

Using this arrangement measurements are simplified and increase of selectivity can be achieved. Further on components can also be determined which don't give in a one step enzyme reaction electroanalytically well determinable product, or change in the concentration or activity of a detectable species. The sensor of the invention can be constructed also that on separated area parts, or on given area part of the natural structured membrane different kinds of enzymes are immobilized in statistically homogeneous distribution and to the mentioned area parts one or more sensing electrodes are contacted. This arrangement enables one to prepare multifunction molecule selective sensors without increase of the dimensions, whereby the analysis of more components can be accomplished simultaneously in the same sample, or by measuring simultaneously the concentration of components interfering with the measurements their effect can be accounted for automatically or in manual way.

In the case of other variation of the molecule selective sensor of the invention e.g. in case of sensors for industrial use in order to protect the reaction layer against mechanical effects and to increase its mechanic stability an inert plastic net or tissue is placed in contact with the natural structured membrane.

At other versions—to achieve very short response time—the immobilized enzyme containing reaction layer is formed in the surface layer of one side of the natural structured membrane while in the surface layer of its other side gas permeable or ion exchanger type layer is formed by a cross linkage method after a previous impregnation process.

The surface of the natural structured membrane is treated with a solution containing the enzyme and bifunctional reagent material e.g. glutaraldehyde capable to form proper chemical linkage. After the completion of the linking reaction the membranes are placed in a bath containing distilled water, where soluble compounds are dissolved. After completion of the dissolution process the membranes are ready to use. After this, in given cases, the metal sensing electrode is prepared. In order to clean it, the surface of the sensing electrode is treated with nitric acid, after which it is rinsed with water. To remove the oxides and the oxygen gas dissolved physically in the metal sensing electrode, it is kept in bath containing reducing agent, e.g. ascorbic acid.

The prepared membrane in given case together with the gas or dissolved component permeable film is placed on the covering body of the sensor, the sensing and the reference electrodes are immersed in the electrolyte solution in the covering body in such a way that the surface of the sensing electrode is in the immediate vicinity of the membrane. The electrodes are fixed and the sensor is read for use.

EXAMPLE 1

FIG. 1 shows—partly intersected—the form prepared according to the Example of the glucose selective sensor of the invention.

In the cave of the covering body 1 is placed the chloride containing electrolyte solution 2 of buffer character, in which immerse the platinum sensing electrode 4—being placed in a supporting body 3—and a silver-silver chloride reference electrode 5.

The end of covering body 1 is closed with gas permeable polypropylene film 6 being in contact with the sensing electrode 4. Membrane of natural origin, commercial hog intestinal membrane 7 containing glucose oxidase (E.C.1.1.3.4) immobilized with glutaric aldehyde is in contact with the gas permeable film 6. Gas permeable film 6 and membrane 7 of natural origin are fixed to the covering body 1 by rubber ring 8. The other end of covering body 1 is closed by electrode cap 9.

Cable 10 contacted with sensing electrode 4 and reference electrode 5 is connected to the inputs of polarizing power source and current intensity measuring circuit.

The preparation of the glucose selective sensor is made on the following way. A given part of the salted commercially available hog intestinal membrane is soaked in distilled water for 10 to 15 minutes. The swollen membrane together with 15μ thick gas permeable e.g. polypropylene membrane is fixed in stretched out state on the end of the covering body of the sensor. (The polypropylene membrane must be on the side of the cave of the covering body.) The membrane is let to dry for 20 minutes. 50 mg. of glucose-oxidase enzyme (E.C. 1.1.3.4.) is dissolved in 0.5 ml. pH=7.4 buffer solution and 25 μl of 25% glutaric aldehyde solution is added to it. 20 μl of the homogenised solution is spread as an even layer on the surface of the membrane. The membrane is let to dry for 20 minutes, after washing with distilled water the free enzyme and the remaining unreacted glutaric aldehyde is removed.

The membrane prepared in this way containing immobilized glucose oxidase is ready for measuring or storage.

After preparing the active membrane the platinum sensing electrode placed in the carrier body in the said way, is prepared, or conditioned. The measuring surface of the sensing electrode is soaked in 6 moles/dm$^3$ nitric acid, dropped on glass plate surface for 2 to 3 minutes. The nitric acid is rinsed with distilled water. After the rinsing the surface of the sensing electrode is soaked in freshly prepared ascorbic acid solution of 2% for 20 to 30 minutes.

After the soaking the ascorbic acid is removed with a distilled water washing. Completing the washing the sensing electrode is ready to measure. (The soaking in nitric acid and in ascorbic acid solution must be repeated in every 2 to 3 weeks during the measurements.)

After the preparatory procedure the glucose selective sensor is put together according to FIG. 1, and it is connected to the polarising power source and galvanometer unit.

The determination of the unknown sample concentration can be done using calibration curve or addition method. In the followings an advantageous version of the addition methods, the serial sample addition method is described.

It has been concluded that between the measured decrease in current intensity ($\Delta i$) and the glucose concentration of the solution (c) the following relationship exists:

$$\Delta i = k \frac{v}{1 + \frac{k}{c}} \quad (1)$$

where
v is the maximal reaction rate,
K the Michaelis constant of the enzyme substrate complex,
k the rate constant.

Measuring the current decrease in two solutions of known glucose concentration the values v and k valid for the given circumstances are determined, on the basis of which the concentration of the solution containing the n-th sample can be calculated from the measured current intensity decrease according to the followings:

$$c_n = i_n k \frac{(c_{n-1} + k)^2}{k + v} \quad (2)$$

On the basis of equation (2) the concentration of the sample is:

$$c'_n = c_n \frac{V_A + \Sigma a_n}{a_n}$$

where
$a_n$ is the volume of the n-th sample,
$V_a$ the volume of the solution after the addition of the standards,
the results obtained with other known methods in case of which the value of scattering often can exceed the 10%.

TABLE I

| concentration of the standard solutions mg % | number of the parallel measurements | the average of the measured data mg % | scattering mg % |
|---|---|---|---|
| 180 | 11 | 180 | ±5 |
| 120 | 11 | 121 | ±3 |
| 90 | 11 | 91 | ±3 |

Other molecule selective sensors also can be prepared according to the method of the Example. In table II a few further examples are shown.

In the first column of the table the molecule selectively measurable with the sensor is given, in the other column the enzyme immobilized in the membrane being in contact with the gas permeable film is listed while in the third one the type of the sensing electrode is given.

TABLE II

| Component can be determined | Immobilized enzyme | Sensing electrode |
|---|---|---|
| uric acid | uricase E.C.1.7.3.3. | platinum |
| cholesterine | cholesterine oxidase E.C.1.1.3.6. | " |
| L-amino- acid | L-amino acid oxidase E.C.1.4.3.2. | " |
| D-amino acid | D-amino acid oxidase E.C.1.4.3.3. | " |
| D-galactose | Galactose oxidase E.C.1.1.3.9. | " |
| sulphite | sulphite oxidase E.C.1.8.3.1. | " |

TABLE II-continued

| Component can be determined | Immobilized enzyme | Sensing electrode |
|---|---|---|
| oxalate | oxalate oxidase E.C.1.2.3.4. | " |
| xanthyne | xanthyne oxidase E.C.1.2.3.2. | " |
| o-diphenol | o-diphenol oxidase E.C.1.10.3.1. | " |
| p-diphenol | p-diphenol oxidase E.C.1.10.3.2. | " |
| hydrogenperoxide | catalase E.C.1.11.1.6. | " |
| lactate | lactate oxidase E.C.1.1.3.2. | " |
| piruvate | piruvate oxidase E.C.1.2.3.3. | " |
| alcohol | alcohol oxidase E.C.1.1.3.1.3. | " |
| L-phenylalanine | phenylalaninase E.C.1.14.3.1. | " |
| 2-oxocarbonic acid | piruvate decarboxylase E.C.4.1.1.1. | hydrogen ion selective electrode e.g. glass electrode |
| oxalic acetate | oxalic acetate decarboxylase E.C.4.1.1.3. | hydrogen ion selective electrode e.g. glass electrode |
| acetoacetic acid | acetoacetate decarboxylase E.C.4.1.1.4. | hydrogen ion selective electrode e.g. glass electrode |
| L-valine | valine decarboxylase E.C.4.1.1.14. | hydrogen ion selective electrode e.g. glass electrode |
| L-glutamate | glutamate decarboxylase E.C.4.1.1.15. | hydrogen ion selective electrode e.g. glass electrode |
| L-ornithine | ornithine decarboxylase E.C.4.1.1.17. | hydrogen ion selective electrode e.g. glass electrode |
| L-lysine | lysine decarboxlase E.C.4.1.1.18. | hydrogen ion selective electrode e.g. glass electrode |
| penicilline | β-lactamase E.C.3.5.2.6. | hydrogen ion selective electrode e.g. glass electrode |

EXAMPLE 2

FIG. 2 shows—partly intersected—the form prepared according to the example of the urea-selective sensor of the invention. Inside covering body 1 is placed electrolyte solution 2 containing chloride ions, in which are immersed sensing electrode 4 and silver-silver chloride reference electrode 5; disc chaped insulating layer 11 fixes sensing electrode 4 in the end of covering body 1 with a bonding impermeable for the electrolyte solution 2, membraneous wall section of air bladder of fish containing enzyme urease (E.C.3.5.1.5.) immobilized with glutaric aldehyde, serving as membrane 7 of natural origin is in contact with sensing electrode 4.

The membrane 7 is fixed to the covering body 1 with rubber ring 8. Inside the wall of covering body 1, filter layer 12 e.g. ceramic bar permeable for electrolyte solution 2 is placed. The other side of covering body 1 is closed with plastic electrode cup 9. Cable 10 connected to sensing electrode 4 and reference electrode 5 is in connection with the inputs of electronic voltage measuring apparatus.

The preparation of the reaction layer of the urea selective sensor is done as it is given in description of Example 1. The only difference is that on the surface of the membrane urease enzyme (E.C.3.5.1.5.) is immobilized and instead of hog intestinal membrane silk or nylon net is used. The sensor is assembled in a manner shown in FIG. 2. The determination of the concentration of the component to be measured can be accomplished using cell voltage-concentration calibration curve or using addition method in the well known way.

Different other molecule selective sensors of the Example 2 also can be accomplished. In Table III are given a few further examples summarized. In the first column of the table the molecule selectively measurable with the sensor is given, in the other column the enzyme immobilized in the membrane is listed while in the third one the type of the sensing electrode to be used is given.

TABLE III

| Component can be determined | Immobilized enzyme | Sensing electrode |
|---|---|---|
| L-dioxyphenyl-alanine | L-amino acid oxidase E.C.1.4.3.2. | Ammonium ion selective electrode |
| L-phenylalanine | L-amino-acid oxidase E.C.1.4.3.2. | Ammonium ion selective electrode |
| L-amino acids | L-amino acid oxidase E.C.1.4.3.2. | Ammonium ion selective electrode |
| D-serine | D-serine dehydratase E.C.4.2.1.14. | Ammonium ion selective electrode |
| L-homoserine | homoserine dehydratase E.C.4.2.1.15. | Ammonium ion selective electrode |
| L-threonine | threonine dehydratase E.C.4.2.1.16. | Ammonium ion selective electrode |
| L-hystidine | hystidinase E.C.4.3.1.3. | Ammonium ion selective electrode |
| nitrite | nitrite reductase E.C.1.6.6.4. | Ammonium ion selective electrode |

EXAMPLE 3

The construction of the arginine selective sensor of the invention prepared according to that example is basically identical with the construction of the urea selective sensor. The difference is that two membranes 7 of natural origin one covering the other are fixed with ring 8 on the end of covering body 1, on the surface of membrane being on sensing electrode 4 side enzyme urease while on the surface of the other membrane perforated enzyme arginase is bound in immobilized form. This way the arginine selective sensor is formed with two reaction layers.

The preparation of the arginine selective sensor of the invention is done in the following way: First the urea selective sensor is prepared as it is given in Example 2. After that on the surface of the urease enzyme containing natural membrane an other natural based perforated membrane prepared from ewe intestine is placed, on the surface of which is formed the reaction layer containing enzyme arginase (E.C.3.5.3.1.). The preparation of the latter is done identically as it is described in Example 1, with the difference that in the buffer solution 10 mg. of albumine is also suspended together with the enzyme.

The preparation of the latter is done identically as it is described in Example 1.

The arginine selective sensor can also be accomplished that way, that for its preparation only one membrane 7 of natural origin is used on the surface of which in statistically homogeneous distribution two kinds of enzymes, arginase and urease are immobilized. In case of this version the further construction and preparation of the sensor consequently are identical with those described at version earlier discussed.

The function of the sensor is based on a two step chemical reaction:

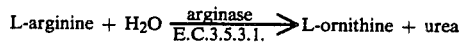

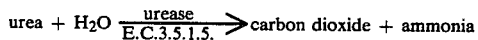

The determination of the concentration of arginine to be measured is done on the well known ways using calibration curve or addition method. A survey is given in table IV about the molecule selective sensors of the invention which can be prepared with two reaction layers or with a reaction layer containing two kinds of enzymes in statistically homogeneous distribution similarly to Example 3. In the first column of the table the molecule which can be determined with the molecule selective sensor, in the second column the enzyme catalyst immobilized in the external membrane can be found. The third column is constructed by the enzyme catalysts immobilized in on the internal membrane being in the side of the sensing electrode. In the fourth column the appropriate sensing electrodes are listed.

TABLE IV

| Component can be determined | Enzyme immobilized first kind | Enzyme immobilized second kind | Sensing electrode |
|---|---|---|---|
| inosine | uridine nucleosidase E.C.3.2.2.2. | xanthine oxidase E.C.1.2.3.2. | platinum electrode |
| adenosine | adenosine nucleoidase E.C.3.2.2.a. | adenine deaminase E.C.3.5.4.2. | ammonium-ion or hydrogen ion selective electrode |
| guanosine | guanosine phosphorilase E.C.2.4.2.15. | guanase E.C.3.5.4.3. | ammonium-ion or hydrogen ion selective electrode |
| guanine | guanase E.C.3.5.4.3. | xanthine oxidase E.C.1.2.3.2. | platinum electrode |
| creatinine | creatininase E.C.3.5.3.3. | urease E.C.3.5.1.5. | ammonium ion selective electrode |
| β-D-glucosids disaccharides amygdaline salicine | β-glucosidase E.C.3.2.1.21. | glucose oxidase E.C.1.1.3.4. | platinum electrode |
| α-D-glucosides e.g. maltose | α-glucosidase E.C.3.2.1.20. | glucose oxidase E.C.1.1.3.4. | platinum electrode |
| D-glucose-1-phosphate | glucose-1-phosphatase E.C.3.1.3.10. | glucose oxidase E.C.1.1.3.4. | platinum electrode |
| D-glucose-6-phosphate | glucose-6-phosphatase E.C.3.1.3.9. | glucose oxidase E.C.1.1.3.1. | platinum electrode |
| barbiturate | barbiturase E.C.3.5.2.1. | urease E.C.3.5.1.5. | ammonium or hydrogen ion selective electrode |

EXAMPLE 4

In the Example 4 the model form and the preparation of the bifunctional molecule-selective sensor is described.

Two platinum sensing electrodes 4 built in carrier body 3 are placed in chloride ion containing electrolyte solution 2 of buffer property being inside of covering body 1. Gas permeable polypropylene film 6 fixed on the opening of covering body 1 is in contact with the surfaces of sensing electrodes 4. The surface of film 6 is covered with fine epidermis film membrane 7 of natural origin.

On that part of the membrane 7 of natural origin which is in contact with the first sensing electrode 4 or on surface part corresponding to that on the opposite side of the membrane 7 enzyme D-amino acid oxidase, while on the other part contacted with the other sensing electrode 4 or on the surface part corresponding to that on the opposite side of the membrane 7 enzyme L-amino acid oxidase is bound in immobilized form.

The construction of the bifunctional molecule selective sensor concerning the further details is consequently similar to that of the sensor described in the Example 1.

The preparation of reaction layer containing amino acid oxidase is done in the following way: The wet epidermis membrane is stretched on the gas permeable polypropylene film. It is let to dry for 30 minutes in room temperature. After this on the first surface part of the membrane 10 μl of a pH=8.3 phosphate buffer solution is spread 0.1 ml. of which contains 5 mg. D-amino acid oxidase enzyme (E.C.1.4.3.3. Sygma product, crystalline) in suspension and 10 μl. of 25% glutaric aldehyde solution is added to it. Following this on the other surface part of the membrane 10 μl. of a pH=6.5 phosphate buffer is spread 0.1 ml. of which contains 10 mg. L-amino acid oxidase enzyme (E.C.1.4.3.2. Sygma product, type IV) in suspension, after this 10 μl. of 25% glutaric aldehyde solution is added to it.

The further steps concerning the preparation of the sensor consequently are identical with those described in Example 1.

With the bifunctional molecule selective sensor described it is possible to determine selectively D- and L-amino acid isomers in samples containing both species. In carrying out the measurement first the selective sensor is calibrated with standard solutions of the first amino acid to be measured, e.g. L-phenylalanine after with that of the other amino acid isomer e.g. D-phenylalanine. To calibrate the electrode the electrode is taken out of a solution of phosphate buffer (pH=8) stirred intensively and deeped in one of the standard solution of the same pH using stirring of the same intensity employing a polarizing voltage of −0.6 V, the change of the current intensity ($\Delta i$) is measured.

Plotting the measured value of $\Delta i$ against the concentrations of the standard solutions the two calibration curves are prepared by means of which the concentrations of the different amino acids, the ratio of the two optical isomers in sample solutions can be determined after measuring $\Delta i$-values.

The use of the selective sensor constructed according to the example is very advantageous in case of studying the effectivity of optical isomers resolving processes.

The addition method described in connection with the Example 1 also can well be used for determination of the ratio of amino acid isomers. Similarly to Example 4 several other advantageously applicable bifunctional molecule selective sensor of the invention can be prepared.

A survey on them is given in table V.

In the second column of the table the name of the enzyme immobilized in the first surface portion is listed, while in the fourth column the enzyme immobilized in the other part of the membrane is given.

TABLE V

| component can be determined | enzyme immobilized in the first part of the membrane | component can be determined | enzyme immobilized in the second part of the membrane |
|---|---|---|---|
| glucose | glucose oxidase E.C.1.1.3.4. | alcohol | alcohol oxidase E.C.1.1.3.1.9. |
| glucose | glucose oxidase E.C.1.1.3.4. | mannose | hexose oxidase E.C.1.1.3.5. |
| urea | urease E.C.3.5.1.5. | creatinine | creatininase E.C.3.5.3.3. urease E.C.3.5.1.5. |
| glucose | glucose oxidase E.C.1.1.3.4. | uric acid | uricase E.C.1.7.3.3. |
| glucose | glucose oxidase E.C.1.1.3.4. | L-phenyl-alanine | phenylalaninase E.C.1.14.3.1. |
| urea | urease E.C.3.5.1.5. | arginine | arginine decarboxylase E.C.4.1.1.19. |
| glucose | glucose oxidase E.C.1.1.3.4. | amygdaline | β-glucosidase E.C.3.2.1.21. glucose oxidase E.C.1.1.3.4. |

EXAMPLE 5

In the Example 5 the construction and the method of preparation of a multifunctional molecule selective sensor of the invention are described as an example which can be used for the selective determination of certain amino acids in the presence of others.

The construction of the multifunctional sensor is similar to that of the bifunctional sensor described in Example 4; it is a difference that it does not contain gas-permeable film 6, furtheron in the electrolyte solution 2 being in covering body 1 three hydrogen ion selective glass sensing electrodes 4 are placed; in the three separated part of the membrane 7 each being in contact with another sensing electrode 4 different selective amino acid decarboxylase; L-lysine decarboxylate, L-thyrosine decarboxylase, L-phenylalanine decarboxylase immobilized enzyme containing reaction layer is formed.

The preparation of the sensor and the reaction layers are made identically to those described in Example 4.

With the selective sensor accomplished as an example the determination of L-thyrosine, L-lysine, L-phenylalanyne content of amino acid containing samples can be made using three different cell voltage-amino acid concentration calibration curve, each of them refers to an other amino acid.

Similarly to the multifunctional sensor described as example different other versions also can be prepared. The different individual reaction layer fields can contain the following enzymes in immobilized form: L-arginine decarboxylase, L-glutamic acid decarboxylase, L-glutamine decarboxylase, L-hystidine decarboxylase, urease.

What we claim is:

1. A hollow molecule-selective sensor having a sensing electrode, a reference electrode and a permeable, enzymatically active membrane comprising a self-supporting, 10–15 micron thick protein membrane found in nature which closes the bottom of the sensor, said membrane containing on its surface the reaction product solely of an enzyme and glutaric aldehyde.

2. A sensor as in claim 6, wherein the said protein membrane is selected from the group consisting of hog intestine membrane, ewe intestine membrane, air bladder of fish, epidermal section of a mammal, epidermal section of a reptile and corneal section.

* * * * *

UNITED STATES PATENT AND TRADEMARK OFFICE
CERTIFICATE OF CORRECTION

PATENT NO. : 4,354,913

DATED : October 19, 1982

INVENTOR(S) : Ernö Pungor et al

It is certified that error appears in the above-identified patent and that said Letters Patent are hereby corrected as shown below:

In claim 2, line 1, "6" should read as -- 1 --.

Signed and Sealed this

Twenty-first Day of December 1982

[SEAL]

Attest:

GERALD J. MOSSINGHOFF

Attesting Officer     Commissioner of Patents and Trademarks